(12) United States Patent
Zhu et al.

(10) Patent No.: US 11,377,501 B2
(45) Date of Patent: Jul. 5, 2022

(54) PEPTIDE HAVING HIGH AFFINITY FOR PD-L1 PROTEIN AND USE THEREOF

(71) Applicants: Naishuo Zhu, Shanghai (CN); Baoxiu Liu, Shanghai (CN)

(72) Inventors: Naishuo Zhu, Shanghai (CN); Baoxiu Liu, Shanghai (CN)

( * ) Notice: Subject to any disclaimer, the term of this patent is extended or adjusted under 35 U.S.C. 154(b) by 3 days.

(21) Appl. No.: 16/488,164

(22) PCT Filed: Jan. 25, 2018

(86) PCT No.: PCT/CN2018/074112
§ 371 (c)(1),
(2) Date: Aug. 22, 2019

(87) PCT Pub. No.: WO2018/153208
PCT Pub. Date: Aug. 30, 2018

(65) Prior Publication Data
US 2021/0230286 A1    Jul. 29, 2021

(30) Foreign Application Priority Data
Feb. 25, 2017    (CN) .......................... 201710105087.2

(51) Int. Cl.
*C07K 1/107*    (2006.01)
*C07K 16/28*    (2006.01)

(52) U.S. Cl.
CPC .......... *C07K 16/2878* (2013.01); *C07K 1/107* (2013.01)

(58) Field of Classification Search
CPC .............................. C07K 16/2878; C07K 1/107
See application file for complete search history.

(56) References Cited

U.S. PATENT DOCUMENTS

2017/0112925 A1*    4/2017    Junttila .............. A61K 31/4523

OTHER PUBLICATIONS

Jones, Pharmacogenomics Journal (2001) 1:126-134. (Year: 2001).*
Tosatto et al., Current Pharmaceutical Design (2006), 12:2067-2086. (Year: 2006).*
Extended Search Report of EP18757780.4 dated Dec. 15, 2020.
First Office Action of JP2019-546150 dated Sep. 9, 2020 (translated).
Chang, et al., "Blocking of the PD-1/PD-L1 Interaction by a D-Peptide Antagonist for Cancer Immunotherapy," Angew Chem Int. Ed., vol. 54, pp. 11760-11764 (2015).
International Preliminary Report on Patentability and Written Opinion of the International Search Authority issued in PCT/CN2018/074112.

* cited by examiner

*Primary Examiner* — Julie Wu
*Assistant Examiner* — Cheom-Gil Cheong
(74) *Attorney, Agent, or Firm* — Elmore Patent Law Group, P.C.; Carolyn Elmore; Joseph Zucchero

(57) ABSTRACT

The present invention provides a peptide having high binding affinity for PD-L1 protein and use thereof. The peptide has an amino acid sequence of SEQ ID NO: 1, SEQ ID NO: 3 or SEQ ID NO: 4, or the peptide is a tandem or branched peptide with a single repeat or multiple repeats of SEQ ID NO: 1, SEQ ID NO: 3 and SEQ ID NO: 4 and has an amino acid sequence of SEQ ID NO: 5. The peptide can bind to human PD-L1 with high affinity, competitively block the affinity of PD-1/PD-L1 protein, block the negative regulatory tolerance pathway of human tumors, activate immunity and increase the lethality of T cells against tumor cells.

6 Claims, 2 Drawing Sheets
Specification includes a Sequence Listing.

PEPTIDE HAVING HIGH AFFINITY FOR PD-L1 PROTEIN AND USE THEREOF

SEQUENCE LISTING

The contents of the ASCII text file Seq List.txt is incorporated herein by reference in its entirety. The file was created Sep. 25, 2019 and the file size is 2 kilobytes.

TECHNICAL FIELD

The present invention belongs to the field of biotechnology. The invention specifically relates to a peptide having high affinity for PD-L1 protein, and use thereof.

BACKGROUND ART

Tumor is a serious disease that threatens human health and is difficult to prevent effectively. At present, the main methods for treating tumors include radiotherapy, chemotherapy and surgical treatment, but the therapeutic effect thereof is not satisfying, and the 5-year survival rate after surgery is low. Currently, development of an effective drug for the treatment of tumors is a hot topic in cancer research. In recent years, immune checkpoint therapy represented by anti-PD-1/PD-L1 has been explored as a new approach for tumor treatment. Three PD-1/PD-L1 antibody drugs have been approved by the US Food and Drug Administration (FDA) for clinical treatment. Although these drugs have certain effects, they have drawbacks such as low efficiency, side effects and off-target. Therefore, it is urgent to develop a drug that is efficient, long-lasting and has a wide range of therapeutic effects.

SUMMARY OF THE INVENTION

The target peptide of the invention is obtained by chemical synthesis and purification. The dissociation constant between the peptide and PD-L1 protein is determined by ELISA, and the blocking effect of the peptide on PD-1/PD-L1 signaling pathway is determined. The affinity of the peptide for PD-L1 protein expressed on the surface of tumor cells was detected by flow cytometry. Finally, the peptide is infused into a mouse tumor model, and the potential value of the peptide in treating tumor is confirmed by the changes in tumor size and survival time of the mouse.

The object of the present invention is to provide a peptide having high binding affinity for PD-L1 protein and use of the peptide in treatment of tumor.

The present disclosure provides a peptide having high affinity for human PD-L1 protein (referred to as PPLC), wherein the peptide has an amino acid sequence as set forth in SEQ ID NO: 1. The peptide has the following functional characteristics: (1) a high affinity for human PD-L1 protein, with a dissociation constant Kd of 0.75 µM (Kd value indicates the concentration of ligand when half of the receptors are bound by the ligand, and the smaller the Kd value, the higher the affinity of the receptor to the ligand); (2) it can effectively block the affinity of PD-1/PD-L1 protein; (3) it can effectively binds to PD-L1 protein expressed on the cell surface; (4) infusion of the peptide into tumor-injected animals can effectively inhibit tumor growth and extend the survival time of animals.

The present disclosure also provides a gene encoding the peptide having high affinity for human PD-L1 protein (consisting of degenerate codons of the corresponding amino acids), wherein the gene has a nucleotide sequence as set forth in SEQ. ID. NO. 2.

The present disclosure also obtains, by biotechnological means, a series of peptide sequences having the same function as the peptide represented by SEQ ID NO: 1, wherein the peptide sequences mainly include SEQ ID NO: 3 and SEQ ID NO: 4.

The present disclosure also provides a peptide, comprising amino acid sequences of peptides having high affinity for PD-L1 protein as set forth in SEQ ID NO: 1, SEQ ID NO: 3 and SEQ ID NO: 4, wherein the peptide is a single repeated or multiple repeated tandem or branched peptide molecular sequence, and a molecular comprising these core sequences (i.e., having a homology of more than 70%), wherein the molecular has an amino acid sequence as set forth in SEQ ID NO: 5.

The present disclosure also provides a peptide modified by biological or chemical group, comprising SEQ ID NO: 1, SEQ ID NO: 3 or SEQ ID NO: 4 of the peptide having high affinity for PD-L1 protein as a core sequence, and its C-terminal (N-terminal or a side-chain group) is linked to an antigen or a drug, or modified by PEG or covalently modified by other molecular groups.

The present disclosure also provides a modified peptide, comprising the above peptide having high affinity for PD-L1 protein, which is labeled with a FITC fluorophore, an isotope, a chemiluminescent group or an enzyme reagent, and the modified peptide can be used for PD-L1 protein detection.

The present disclosure also provides the use of the above peptide having high affinity for PD-L1 protein in preparation of a PD-L1 protein antagonist.

The present disclosure also provides the use of the above peptide having high affinity for PD-L1 protein in preparation of an agent for detection or for clinical testing of PD-L1 protein expression.

The present disclosure also provides the use of a gene having nucleotide sequence as set forth in SEQ. ID NO. 2 in preparation of a PD-L1 protein antagonist or preparation of an agent for tracer detection of PD-L1 protein.

The peptide of the present invention having the amino acid sequence of SEQ ID NO: 1 can be used as a PD-L1 protein antagonist drug. The peptide has a high binding affinity for PD-L1 protein, blocks the negative regulatory signaling pathway PD-1/PD-L1 of human immunity and thus activates immunity, initiates the killing effect of T cells on tumors, and can be used as a potential drug for tumor targeted therapy. The peptide of present invention having the amino acid sequence of SEQ ID NO: 3 or SEQ ID NO: 4 can also be used as an antagonist of PD-L1 protein. These peptides also have a high binding affinity for PD-L1 protein, block the affinity of PD-1/PD-L1 and initiate immunity to kill tumor cells.

Affinity Assay of PPLC Peptide to PD-L1 Protein.

A 96-well ELISA plate was coated with 2 µg/ml PD-L1 protein at 4° C. overnight. Different concentrations of PPLC peptide labeled with FITC were added to each well and incubated for 1 h. After incubation, HRP-conjugated anti-FITC antibody was added, incubated for 1 h, and then ABTS coloring solution was added. The OD value at 410 nm was measured using a M5 microplate reader, and GraphPad Prism 6 was used for plotting and analysis. The results demonstrate that PPLC peptide has a strong affinity for PD-L1 protein, with a dissociation constant Kd of 0.75 µM (FIG. 1).

Competitive Binding Assay Between PPLC Peptide and PD-1 to PD-L1 Protein.

A 96-well ELISA plate was coated with 2 μg/ml PD-L1 protein at 4° C. overnight. Different concentrations of PPLC peptide and 1 μg/ml PD-1 protein were mixed and incubated together. After incubation, rabbit anti-human PD-1 monoclonal antibody was added as primary antibody, and then HRP-conjugated goat anti-rabbit IgG monoclonal antibody was added as secondary antibody. After ABTS color development, the OD value at 410 nm was measured using a M5 microplate reader, and GraphPad Prism 6 was used for plotting and analysis. The results demonstrate that PPLC peptide can effectively block the binding of PD-1/PD-L1 (FIG. 2).

Binding Assay of PPLC Peptide to PD-L1 Protein Expressed on the Cell Surface.

The recombinant plasmid expressing recombinant human PD-L1 protein was transfected into CHO cell line and incubated for 36 hours. After incubation, anti-PD-L1 monoclonal antibody or PPLC peptide labeled with FITC was added and incubated at 4° C. for 30 minutes. After incubation, flow cytometry was performed (FIG. 3). After transfection of the plasmid, the cells were further cultured for 36 hours, and then the PPLC peptide labeled with FITC was added and incubated at 37° C. for 30 minutes. After incubation, fluorescence confocal detection was performed (FIG. 4). The results demonstrate that the PPLC peptide can efficiently bind to the PD-L1 protein expressed on the cell surface (FIG. 3 and FIG. 4).

Effect of PPLC Peptide on Tumor Volume in Animal Tumor Models.

The experimental animals were divided into two groups: PBS group and PPLC group. Tumors were injected subcutaneously into 6 weeks old female Balb/c mice. Two weeks later, when the tumor size reached 100 mm$^3$, PPLC drug treatment was performed. The size of the mouse tumor was measured daily and the change was recorded. The results demonstrate that PPLC peptide can significantly reduce the growth rate of mouse tumor (FIG. 5) and prolong the survival time of mice (FIG. 6).

It can be seen that the peptide provided herein has a strong affinity for PD-L1 protein and can block the affinity of PD-1/PD-L1 protein in human. Thus, the peptide can break the immune tolerance of tumors, activate immunity, initiate killing effect of T cells on tumors, and achieve the purpose of tumor treatment. Therefore, the peptide can be used as a drug for tumor targeted therapy. Since the PPLC peptide has high affinity for PD-L1 protein, it can be used to prepare a probe for detecting PD-L1 protein. When the PPLC peptide is labeled with a FITC fluorophore, an isotope, a chemiluminescent group or an enzyme reagent, it can be used for quantitative, qualitative and location detection of the presence of PD-L1 protein in various biological samples and cells.

DETAILED DESCRIPTION OF THE EMBODIMENTS

Figure 1:
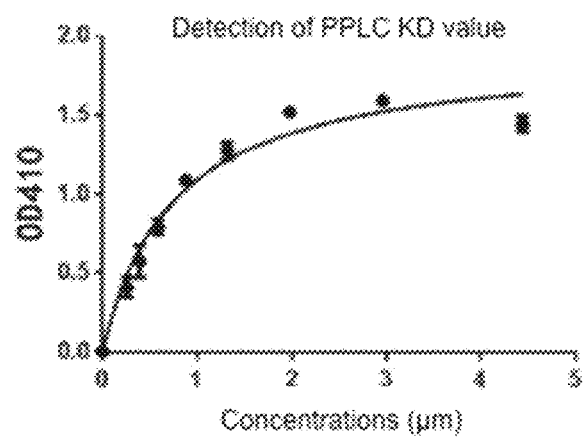
FIG. 1 shows the binding affinity of PPLC peptide to PD-L1 protein.

1. Acquisition and Modification of Peptide Sequences

Desired peptides having an affinity for PD-L1 protein and blocking the affinity of PD-1/PD-L1 protein were artificially synthesized by a chemical method.

2. Synthesis and Purification of the Peptide

Lys (Dde)-Wang Resin was soaked in DCM for 10 min, and then DCM was drained. 25% piperidine (piperidine/DMF) with 3-fold volume was added into the resin, and then the piperidine was drained after bubbling with nitrogen for 20 min. DMF was added and blown for 1 min. After 6 cycles, DMF was drained, and the resin was detected to be blue by ninhydrin. The product is H-Lys (Dde)-Wang Resin. Three equivalents of Fmoc-Val-OH, HATU, DIEA in DMF were added to the resin. After blowing for 20 min with nitrogen, the DMF reaction solution was drained. DMF was added and blown for 1 min with nitrogen before draining. After 3 cycles, the resin was detected to be transparent by ninhydrin. The product is Fmoc-Val-Lys (Dde)-Wang Resin. The crude product was obtained by the same method. Purification was carried out on a Hanbang YCM C18 column using acetonitrile and Milli-Q water. In this way, a peptide having high specificity and high activity was obtained.

3. The Affinity of PPLC Peptide for PD-L1 Protein and Animal Experiment Results (1) Affinity of PPLC to PD-L1 Protein.

A 96-well ELISA plate was coated with 2 μg/ml PD-L1 protein at 4° C. overnight. Different concentrations of PPLC peptide labeled with FITC were added to each well and incubated for 1 h. After incubation, HRP-conjugated anti-FITC antibody was added, incubated for 1 h, and then ABTS coloring solution was added. The OD value at 410 nm was measured using a M5 microplate reader, and GraphPad Prism 6 was used for plotting and analysis. The results demonstrate that PPLC peptide has a high binding affinity for PD-L1 protein, with a dissociation constant Kd of 0.75 μM.

(2) Competitive Binding Assay Between PPLC Peptide and PD-1 to PD-L1 Protein.

A 96-well ELISA plate was coated with 2 μg/ml PD-L1 protein at 4° C. overnight. Different concentrations of PPLC peptide and 1 μg/ml of PD-1 protein were mixed and incubated together. After incubation, rabbit anti-human PD-1 monoclonal antibody was added as primary antibody, and then HRP-conjugated goat anti-rabbit IgG monoclonal antibody was added as secondary antibody. After ABTS color development, the OD value at 410 nm was measured using a M5 microplate reader, and GraphPad Prism 6 was used for plotting and analysis. The results demonstrate that PPLC peptide can effectively block the binding of PD-1/PD-L1.

(3) Binding Assay of PPLC Peptide to PD-L1 Protein Expressed on the Cell Surface.

The recombinant plasmid expressing recombinant human PD-L1 protein was transfected into CHO cell line and incubated for 36 hours. After incubation, anti-PD-L1 monoclonal antibody or PPLC peptide labeled with FITC was added, and incubated at 4° C. for 30 minutes. After incubation, flow cytometry was performed. After transfection of the plasmid, the cells were further cultured for 36 hours, and then the PPLC peptide labeled with FITC was added, and incubated at 37° C. for 30 minutes. After incubation, fluorescence confocal detection was performed. The results demonstrate that the PPLC peptide can efficiently bind to the PD-L1 protein expressed on the cell surface.

(4) Effect of PPLC Peptide on Tumor Volume in an Animal Tumor Model.

The experimental animals were divided into two groups: PBS group and PPLC group. Tumors were injected subcutaneously into female Balb/c mice. Two weeks later, when the tumor size reached 100 mm$^3$, PPLC drug treatment was performed. The size of the mouse tumor was measured daily and the change was recorded. The results demonstrate that PPLC peptide can significantly reduce the growth rate of mouse tumor and prolong the survival time of mice.

Figure 2:
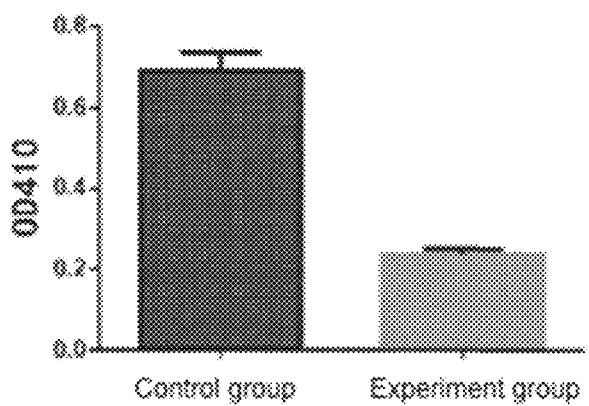
FIG. 2 shows the blockage of the binding of PD-1/PD-L1 protein by PPLC.
Figure 3:
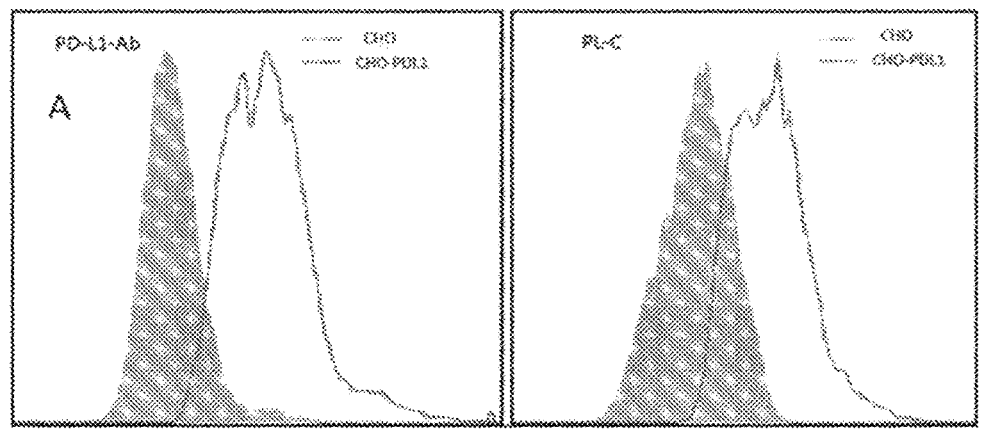
FIG. 3 shows the results of flow cytometry. The left panel shows the results of PD-L1 monoclonal antibody (PD-L1-Ab) detection, and the right panel shows the results of peptide PPLC detection. Gray shades represent PD-L1 negative control cells, red and blue lines represent PD-L1-positive CHO-PDL1 expressing cells.
Figure 4:
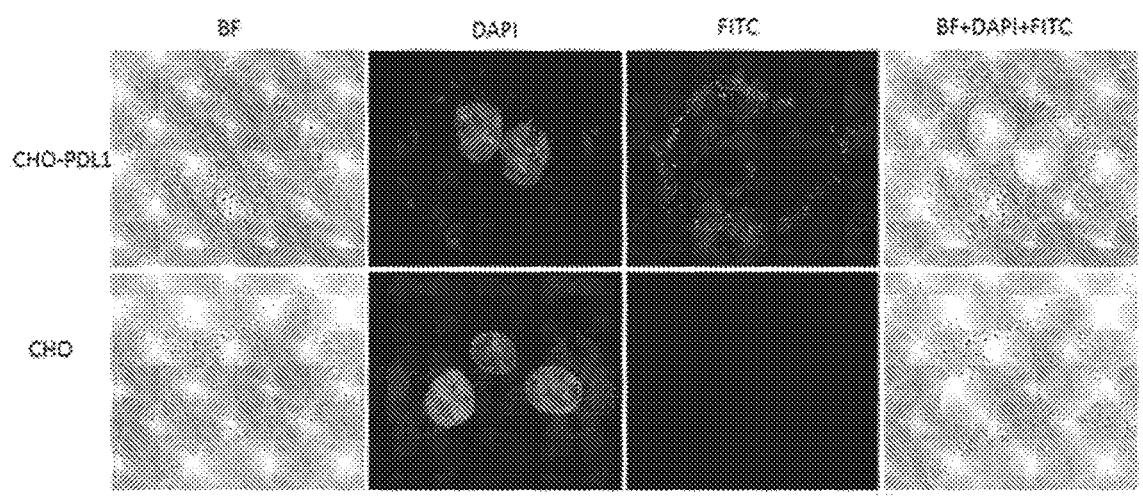
FIG. 4 shows the results of fluorescence confocal assay. The upper right panel shows the results obtained by confocal microscopy showing that the FITC-labeled PPLC has a high affinity for PD-L1 expressed on the surface of CHO cells.
Figure 5:
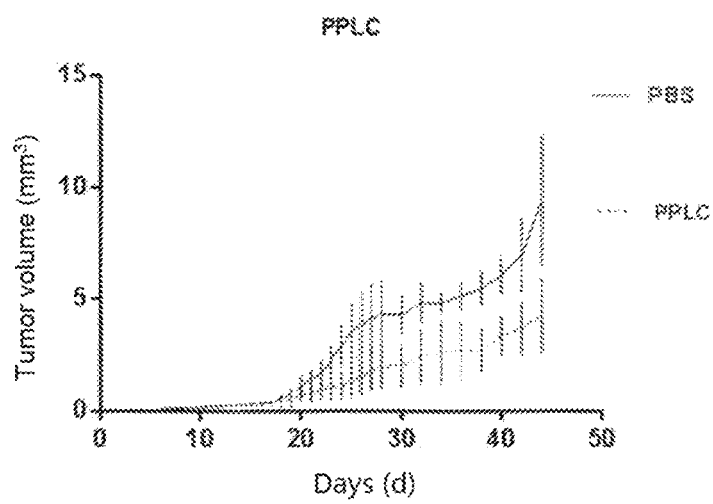
FIG. 5 shows that PPLC peptide inhibits tumor growth in mice.
Figure 6:
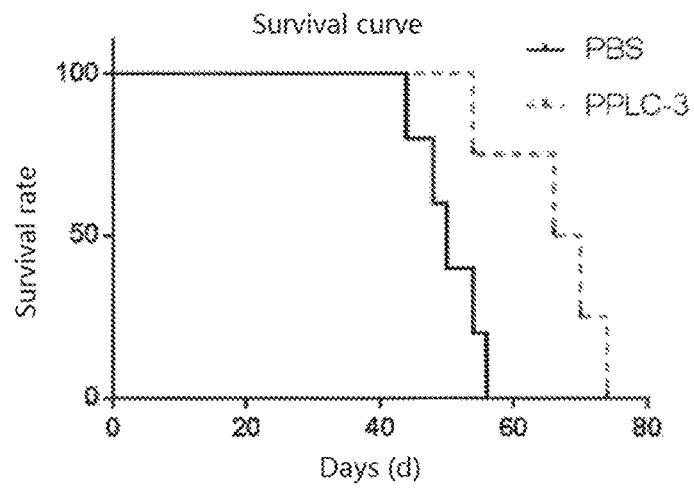
FIG. 6 shows that PPLC peptide prolongs the survival time of mouse.

As shown in FIG. 1 to FIG. 6, PPLC peptide has a high binding affinity for PD-L1 protein, and can block the affinity of PD-1/PD-L1 protein at molecular level. Animal results showed that the tumor size of mice treated with PPLC peptide was significantly smaller than that of the control group. The above results indicate that PPLC peptide can break immune tolerance of tumor, improve the killing of tumor cells by T cells, and thus achieve the purpose of treating tumors.

4. Industrial Applicability

Tumor immunotherapy is a new method for treating tumors developed in recent years. Immune checkpoint blockade therapy represented by PD-1/PD-L1 protein is an important component of tumor immunotherapy. At present, some PD-1/PD-L1 antibody-based drugs have been approved by the FDA, and have shown good results in clinical use and in treatment of diseases such as melanoma. However, at the same time, antibody therapy also faces many problems such as high immunogenicity, high cost, severe side effects and off-target. The development of an anti-tumor drug with both targeting and small immunogenicity is an important direction in the development of immunology today. The peptide having high binding affinity for PD-L1 protein provided herein can inhibit the binding of PD-1/PD-L1 protein, break immune tolerance of tumor and significantly inhibit the growth of tumor cells. Thus, the peptide of the present invention can be used as a potential drug for targeted tumor therapy. In addition, the modified PPLC peptide can be used as a detection reagent for detecting the expression of human PD-L1 protein.

The invention claimed is:

1. A peptide having high affinity for human PD-L1 protein, comprising the amino acid sequence of SEQ ID NO: 1 or SEQ ID NO: 5.

2. A gene encoding the peptide having high affinity for human PD-L1 protein according to claim 1.

3. A peptide modified by biological or chemical group, comprising the peptide having high affinity for human PD-L1 protein according to claim 1 as a core sequence, and wherein its C-terminus, N-terminus or a side-chain group is modified by PEG or covalently modified by other molecular groups.

4. A modified peptide, comprising the peptide having high affinity for human PD-L1 protein according to claim 1, wherein the modified peptide is labeled with a FITC fluorophore, an isotope, a chemiluminescent group or an enzyme reagent, and wherein the modified peptide is used for PD-L1 protein detection.

5. A method for detection or for clinical testing of PD-L1 protein expression, the method comprising administering the peptide having high affinity for human PD-L1 protein according to claim 1 to detect the presence of PD-L1 protein in biological samples.

6. A method for treating a tumor, the method comprising administering a therapeutically effective amount of the peptide having high affinity for human PD-L1 protein according to claim 1 to a subject who can obtain therapeutic benefit by blocking PD-1/PD-L1 signaling pathway.

* * * * *

SEQUENCE LISTING

```
<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Val Ser Val Ser His Phe Gln Lys Val Trp Val Val
1               5                   10

<210> SEQ ID NO 2
<211> LENGTH: 45
<212> TYPE: DNA
<213> ORGANISM: Artificial Sequence
<220> FEATURE:
<223> OTHER INFORMATION: Synthetic

<400> SEQUENCE: 2
gtgagtgtgt cgcattttca gaaggtttgg gttgtgggtg gaggt               45

<210> SEQ ID NO 3
<211> LENGTH: 12
<212> TYPE: PRT
<213> ORGANISM: Artificial Sequence
<220> FEATURE:
<223> OTHER INFORMATION: Synthetic

<400> SEQUENCE: 3

His Glu Ser Trp Leu Pro Ala Tyr Val Leu Gly Ser
1               5                   10
```

```
<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

His Thr Ser Trp Ile Leu Tyr Gly Glu Thr Gly Trp
1               5                   10

<210> SEQ ID NO 5
<211> LENGTH: 40
<212> TYPE: PRT
<213> ORGANISM: Artificial Sequence
<220> FEATURE:
<223> OTHER INFORMATION: Synthetic

<400> SEQUENCE: 5

Val Ser Val Ser His Phe Gln Lys Val Trp Val Val Asp Met His Glu
1               5                   10                  15

Ser Trp Leu Pro Ala Tyr Val Leu Gly Ser Asp Met His Thr Ser Trp
            20                  25                  30

Ile Leu Tyr Gly Glu Thr Gly Trp
            35                  40
```